United States Patent [19]
Stearns

[11] Patent Number: 6,095,811
[45] Date of Patent: Aug. 1, 2000

[54] GRIPPING HANDLE FOR DIAGNOSTIC INSTRUMENT

[75] Inventor: Scott S. Stearns, Marietta, N.Y.

[73] Assignee: Welch Allyn, Inc., Skaneateles Falls, N.Y.

[21] Appl. No.: 09/238,041

[22] Filed: Jan. 27, 1999

[51] Int. Cl.[7] ................................ A61C 1/00; A61C 3/00
[52] U.S. Cl. ............................ 433/29; 433/116; 600/121; 600/125
[58] Field of Search ............................ 433/29, 115, 116; 600/121, 122, 125

[56] References Cited

U.S. PATENT DOCUMENTS

| | | |
|---|---|---|
| 4,693,871 | 9/1987 | Geller . |
| 4,723,912 | 2/1988 | Nieusma . |
| 4,757,381 | 7/1988 | Cooper et al. . |
| 4,810,194 | 3/1989 | Snedden . |
| 4,823,949 | 4/1989 | Bala . |
| 4,846,334 | 7/1989 | Cargould . |
| 4,878,485 | 11/1989 | Adair . |
| 5,010,876 | 4/1991 | Henley et al. . |
| 5,069,337 | 12/1991 | Bala . |
| 5,107,988 | 4/1992 | Bala . |
| 5,154,164 | 10/1992 | Chikama . |
| 5,415,157 | 5/1995 | Welcome . |
| 5,487,661 | 1/1996 | Peithman . |
| 5,490,781 | 2/1996 | Wade . |
| 5,685,822 | 11/1997 | Harhen . |
| 5,807,107 | 9/1998 | Bright et al. ............................ 433/116 |
| 5,865,621 | 2/1999 | Calderwood ............................ 433/116 |
| 5,893,712 | 4/1999 | Stone et al. ........................ 433/116 X |
| 5,921,776 | 7/1999 | Heilbrunn ............................... 433/116 |

*Primary Examiner*—Nicholas D. Lucchesi
*Attorney, Agent, or Firm*—Wall Marjama Bilinski & Burr

[57] ABSTRACT

A gripping handle for a diagnostic instrument, such as an intraoral dental camera, in which the instrument includes an elongate body having an integral camera head and a protective sheath having a transparent window which overlays the camera head. The gripping handle is a unitary hollow section of an elastomeric material which is fitted over a portion of the instrument body and clamps the sheath in a predetermined position to prevent the sheath and the transparent window form being twisted during use. Preferably, the gripping handle and the instrument body can each be made from a biodegradable and recyclable material allowing one time use of each.

5 Claims, 2 Drawing Sheets

GRIPPING HANDLE FOR DIAGNOSTIC INSTRUMENT

FIELD OF THE INVENTION

This invention relates to diagnostic apparatus, and in particular to a gripping handle which is releasably attachable to the body portion of a diagnostic instrument.

BACKGROUND OF THE INVENTION

Diagnostic apparatus, such as endoscopes, are conventionally known and used for medical purposes. Typically, an elongated tubular or other shaped instrument body includes a insertion portion having viewing optics contained therein for allowing inspection of a subject of interest. In use, the insertion portion is directed through a surgical incision or other means into a body cavity, such as the colon, intestines, etc., allowing a disorder or other target of interest to be viewed. Nonmedical devices, such as borescopes, are used in a similar manner for inspection purposes, such as within enclosed pressure vessels, within aircraft or other structures limiting normal vision thereof.

Other known medical diagnostic devices include intraoral dental cameras which include a micro-video camera retained within the distal head of an elongated instrument body that is sized for insertion into the mouth of a patient. The micro-video camera includes a viewing lens portion which focuses an optical image onto a solid-state imager, such as a CMOS or CCD. An electrical signal is then relayed to processing circuitry which converts the signal into a monitor-ready video signal further relayed to a video monitor or other processing apparatus for providing real-time diagnostic analysis.

There is a specific and urgent need to provide a clean and sterile camera surface to the patient for prudent medical reasons. This need is heightened because there is typically bleeding in even the most routine of dental procedures, by which transmission of Hepatitis B, AIDS, etc, might occur if the instrument is not properly handled between patients. Because of the design of the instrument, it is preferable that the camera head, as well as the tubular instrument body, be properly cleaned due to the proximity to the mouth of the patient.

Sterilization is an option in which the instrument is dipped in a liquid bath containing a sterilization agent after use. Application of heat using an oven or other specialized apparatus is still another option. Each of such techniques, however, is time-consuming and may also affect the useful life of the instrument, which contains sensitive electronics and optics. Therefore, a protective flexible sheath, made from polyethylene or other suitable material such as those described in U.S. Pat. No. 4,757,381, has been developed which is sized to encase the tubular instrument body, including the distal camera head. The sheath includes a transparent viewing window to allow the lens portion of the camera to adequately view the subject area after the sheath has been attached.

In use, however, dentists or hygienists using the intraoral camera are required to grip the sheathed tubular instrument body in order to then inspect areas of a patient's mouth. Due to the loose fitting of the sheath to the instrument body, there are instances in which the sheath and/or the instrument is twisted, making support of the instrument difficult and invariably causing the viewing window of the sheath to be shifted from the field of view of the lens portion of the camera, producing unfavorable results.

The aforementioned '381 patent attempts to correct this problem in a number of ways, including heat shrinking a portion of the sheath to tighten the fit of the sheath onto the camera head. Alternative methods include applying a vacuum to the sheath or using fluid pressure to control the positioning of the sheath window in the vicinity of the camera lens. None of these methods are particularly convenient, nor do they aid in providing support for the user of the instrument.

U.S. Pat. No. 5,893,712 solves a number of the above-stated problems. Referring to FIG. 1, this reference describes the use of a hinged or two piece clam shell handle assembly which is fitted over the outer periphery of the instrument body and can be used to trap the sheath therebetween. Though this assembly is effective, it is costly to manufacture in relation to the cost of the instrument, which due to the advent of improved electronics and material manufacturing, can be made quite cheaply.

Therefore, there is a need to provide a gripping handle, such as for an intraoral dental camera or other diagnostic instrument, which is inexpensive to manufacture. There is a further need, particularly in the case of intraoral dental cameras, to provide an inexpensive gripping handle which allows a loosely fitted flexible protective sheath to be effectively supported to prevent twisting thereof and which is easy to attach and remove from the camera.

SUMMARY OF THE INVENTION

It is a primary object of the present invention to provide a flexible gripping handle for an intraoral dental camera or other diagnostic instrument which overcomes the disadvantages of the prior art.

It is another primary object of the present invention to provide an inexpensive gripping handle which allows a protective sheath to be securably and adequately positioned while assisting the dentist, dental hygienist or other user.

Therefore, according to a preferred aspect of the present invention, there is provided a diagnostic instrument assembly comprising:

an elongated instrument body; and a gripping sleeve releasably attachable to at least a portion of said elongated instrument body, said gripping sleeve being a unitary member made from a flexible material and having an inner cavity therethrough sized for tightly fitting over at least a portion of the outer periphery of said elongated instrument body.

Preferably, the sleeve can be slid over one end of the instrument body and positioned at a predetermined position along the length thereof, the sleeve preferably being made from an elastomeric material.

According to another preferred aspect of the present invention, there is provided a diagnostic camera assembly comprising:

an elongated instrument body having a distal camera head;

a flexible protective sheath for loosely covering at least a portion of the assembly, said sheath including a transparent window for allowing viewing access by said camera head, and a unitary flexible sleeve releasably attachable to at least a portion of said elongated instrument body for clamping said sheath in a predetermined position, so as to prevent said window from being moved relative to said camera head during use.

Preferably, the gripping sleeve is made from an elastomeric or sufficiently flexible material which can form fitted over a portion of the elongated instrument body.

An advantage in providing a gripping handle as described is that the diagnostic camera can be reliably supported during use, despite the presence of a loose fitting protective sheath.

A further advantage of the present invention is that the gripping handle can be easily and releasably attached to and removed from the diagnostic instrument, thereby allowing rapid reuse of the instrument without interfering with the removal of the protective sheath.

Alternately, the sleeve can be fabricated from a biodegradable material, allowing the sleeve to be a single use component either along with or separately from the instrument.

A further advantage of the present invention is that by providing a gripping handle as described, the instrument can be used without fear of twisting the protective sheath, thereby allowing the camera to be used in a reliable manner.

These and other advantages, aspects, and features of the present invention are herein presented with reference to the following Detailed Description of the Preferred Embodiments and the following drawings.

DETAILED DESCRIPTION OF THE INVENTION

The present invention is herein described with reference to certain preferred embodiments relating to an intraoral dental camera assembly. It will be readily apparent, however, that the description herein is suitable for other diagnostic apparatus, medical or otherwise.

Figure 1:
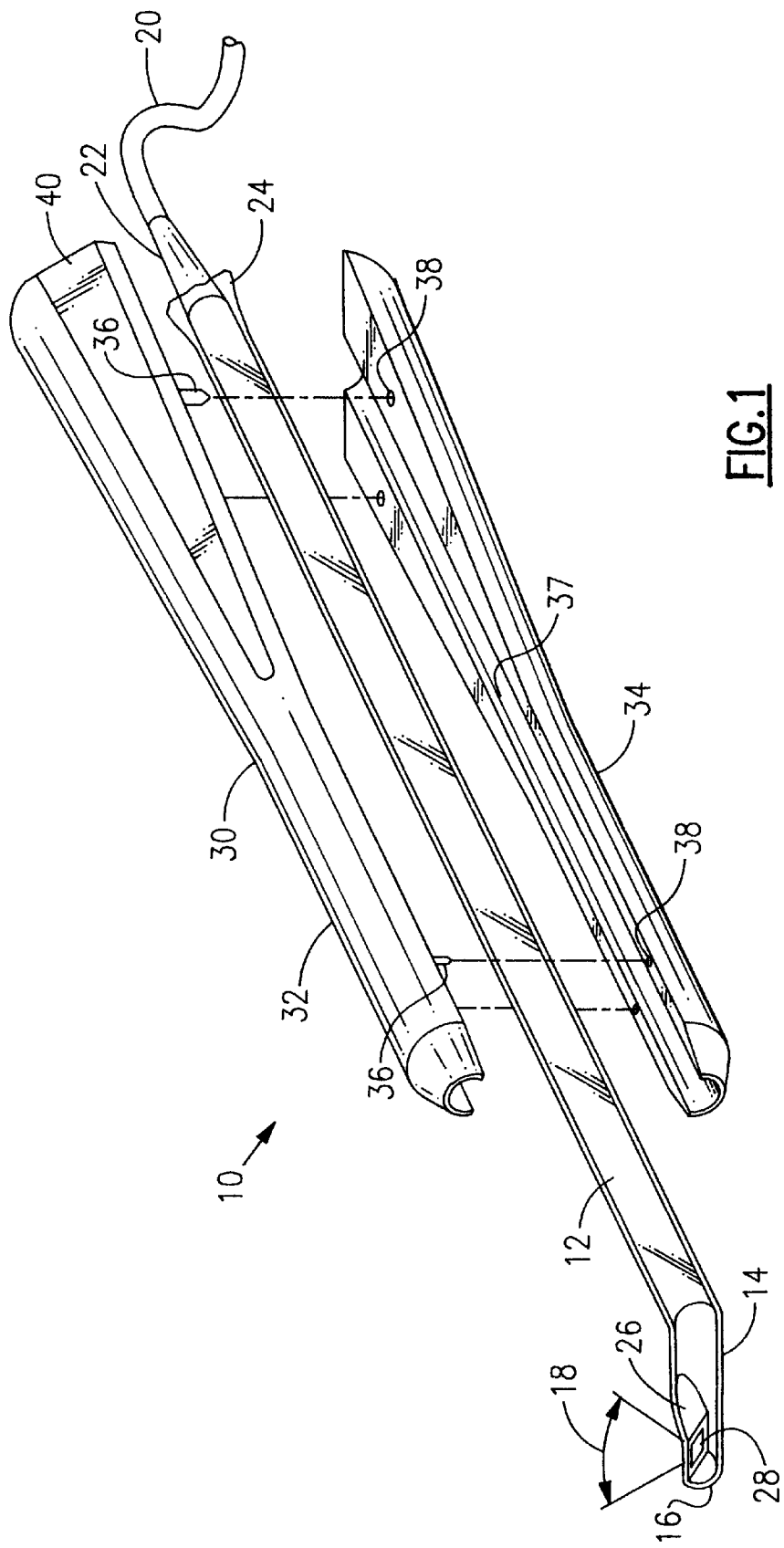
FIG. 1 is a partial top perspective view of an intraoral dental camera assembly having a releasable gripping handle made in accordance with the prior art.

Referring to FIG. 1, an intraoral dental camera assembly 10 is shown in combination with a known gripping handle described in allowed U.S. Pat. No. 5,893,712, the contents of which are incorporated by reference herein. The dental camera assembly 10 includes a tubular or cylindrically shaped elongate instrument body 12 having a camera head 14 located at a distal end 16. The head 14 is preferably angled relative to the remainder of the body 12 to allow a micro-video camera disposed within the head 14 to define a field of view 18 through a lens or window portion 28. It should be noted that only the lens portion 28 has been illustrated, though cameras of the type herein described are known, such as described in U.S. Pat. No. 4,757,381, the entire contents of which are hereby incorporated by reference. A cable 20 extends from the proximal end 22 of the instrument body 12 to transmit images from the micro-video camera to a video monitor (not shown) in a known manner. The details of the workings of the video camera and video processing apparatus are essentially known to those of ordinary skill in the art and do not necessarily form an essential part of the present invention. Therefore, a detailed discussion is not provided, except as required.

A protective sheath 24 is slipped over the distal end 16 of the instrument body 12 as shown, covering the majority of the instrument. The sheath 24 is preferably made from a flexible rubber or plastic material, such as polyethylene or latex, and includes a viewing window 26 which serves to cover the lens portion 28 such that the sheath does not significantly impede the transmission of light to and from the camera head of the instrument. The viewing window 26 is typically made from a clear acrylic.

As noted, the sheath 24 loosely covers the instrument body 12 so that twisting of the sheath occurs as a result of varying finger pressure during actual use. Twisting of the sheath 24 can shift the position of the viewing window 26 and therefore block the transmission of light from the lens portion 28 of the camera assembly 10.

Still referring to FIG. 1, the known gripping handle 30 includes a pair of tapered half sections 32, 34, each half section having a curved interior surface and defining an inner cavity 37 sized for retaining the outer periphery of the tubular instrument body 12 and the sheath 24. One of the half sections 32 includes a set of pins 36 for engaging corresponding holes 38 provided on the interior surface of the remaining half section 34. Either or both of the half sections 32, 34 can further include flattened portions 40 to assist in gripping the assembled handle 30.

In operation, and prior to inserting the assembly 10 into the mouth of a patient (not shown), the protective sheath 24 is placed over the distal end 16 of the instrument body 12 and the viewing window 26 of the sheath is substantially aligned with the lens portion 28 of the contained micro-video camera. The gripping handle 30 is then releasably assembled to the tubular instrument body 12 by aligning the pins 36 with the corresponding holes 38, thereby snapping the handle into tight engagement with the sheath 24, preventing substantial twisting thereof. The handle 30 can be similarly removed following examination, allowing removal of the sheath 24.

Figure 2:
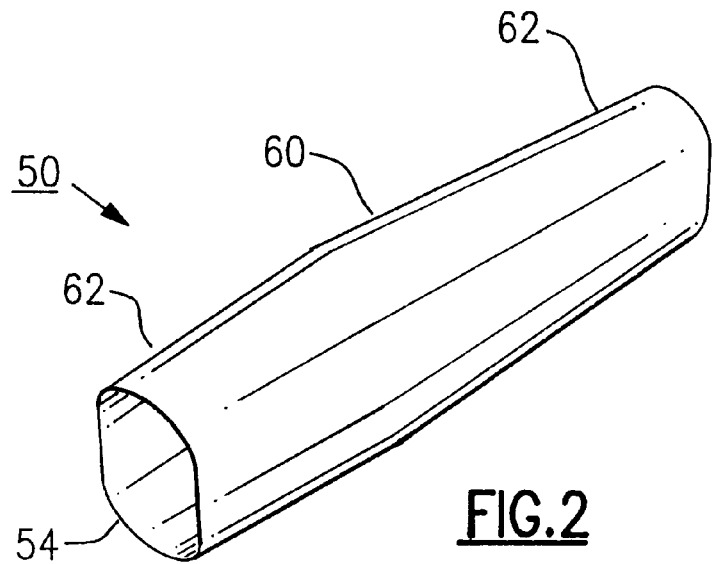
FIG. 2 is a top perspective view of a gripping sleeve made in accordance with a preferred embodiment of the present invention.
Figure 3:
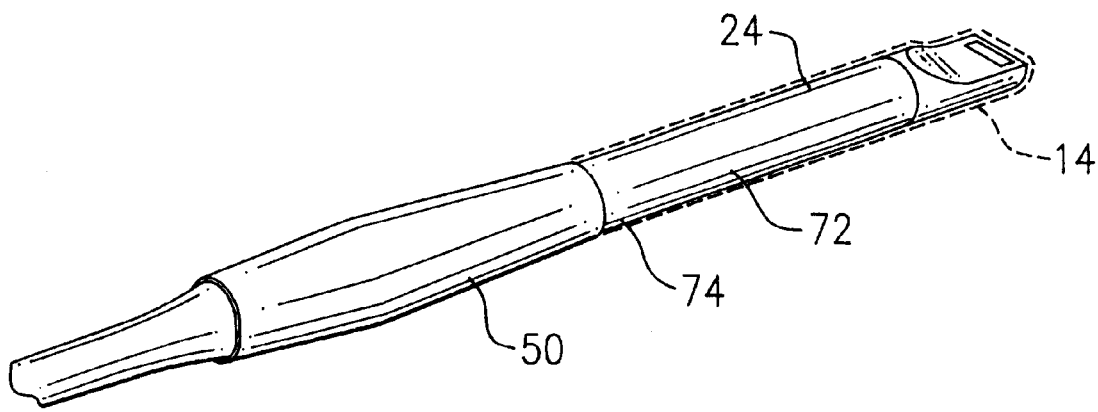
FIG. 3 is a top perspective view of an intraoral dental camera having the gripping sleeve of FIG. 2.

Referring to FIGS. 2 and 3, a gripping handle made in accordance with a preferred embodiment of the present invention is herein described. Similar parts will be described using the same reference numerals for the sake of clarity. In terms of the invention, the gripping handle is a unitary hollow sleeve member 50 made from an elastomeric material, such as vinyl tubing or other suitably flexible material which is appropriately sized such that the inner diameter 54 of the sleeve member is no larger than the corresponding diameter of a portion of interest of a diagnostic instrument body 72 onto which the sleeve member is then assembled. In this instance, the instrument body 72 includes a tapered cross-section which expands from the distal end 14 thereof to a fattened section 74.

According to the present embodiment, the exterior surface 58 of the sleeve member 50 is tapered inwardly from a center portion 60 thereof toward each respective opposing end 62 to facilitate gripping by the user, the exterior surface of the sleeve member so providing a cushioned portion for gripping thereof. Alternately, literally any convenient shape can be selected for the sleeve member 50, providing that the inner diameter 54 thereof is no larger than the corresponding diameter of the instrument body 72 to which the sleeve member is to be attached. Preferably, the inner diameter 54 is slightly smaller than the outer diameter of the remainder of the camera assembly (instrument body 72 and attached sheath 24) so as to allow the elastomeric sleeve member 50 to tightly engage the sheath via a friction fit.

The sleeve member 50 is assembled by placement over the distal end 14 of the assembly and sliding the sleeve member to a predetermined gripping location, such as shown in FIG. 3, after the sheath 24, shown in phantom in FIG. 3, has first been assembled in a similar manner.

Following use, the sleeve member 50 can be slidingly removed from the distal end 14 of the instrument body 72.

The used protective sheath 24 can then be discarded, and the handle either also discarded or sterilized for future use.

Alternately, and depending on the instrument used, the sleeve member 50, sheath 24, and instrument body 72 can be discarded all at once as a single-use or disposable assembly.

It should be readily apparent that other variations or modifications of the described embodiments are possible to provide attachment and release of a gripping sleeve/handle to other diagnostic instruments, even those not requiring a protective sheath.

It should also be apparent that other configurations can be imagined in which the gripping handle can be constructed to cover all or a portion of an instrument body member, and in which the instrument body can assume alternate cross sections, in addition to the tapered, cylindrical or tubular configurations described herein, or including contours, finger grooves, ridges, etc. to aid in gripping.

| PARTS LIST FOR FIGS. 1–3 | |
|---|---|
| 10 | intraoral dental assembly |
| 12 | elongated instrument body |
| 14 | head-camera |
| 16 | distal end |
| 18 | field of view |
| 20 | cable |
| 22 | proximal end |
| 24 | protective sheath |
| 26 | viewing window |
| 28 | lens portion |
| 30 | gripping handle |
| 32 | half section |
| 34 | half section |
| 36 | pins |
| 37 | inner cavity |
| 38 | holes |
| 40 | flattened portions |
| 50 | sleeve member |
| 54 | inner diameter |
| 58 | exterior surface |
| 60 | center portion |
| 62 | ends |
| 72 | instrument body |
| 74 | fattened section |

While this invention has been explained with reference to the structure disclosed herein, it is not confined to the details set forth and this application is intended to cover any modifications and changes within the scope of the following appended claims.

What is claimed is:

1. A diagnostic instrument assembly comprising:

an elongated instrument body having a distal camera head;

a flexible protective sheath for loosely covering at least a portion of said instrument body including said distal camera head, said sheath including at least one transparent window for allowing viewing access by said camera head; and a gripping handle made from a single section of an elastomeric material, said gripping handle being releasably attachable to at least a portion of said elongated instrument body for clamping said protective sheath in a predetermined position, so as to prevent said at least one transparent window from being shifted relative to said camera head wherein said gripping handle is a hollow tubular member having an inner diameter which is smaller than the outer dimension of said elongated instrument body such that said gripping handle is expandably form fitted over said sheath and said body.

2. An assembly as recited in claim 1, wherein said instrument body is that of an intraoral dental camera.

3. An assembly as recited in claim 1, wherein said gripping handle is disposable.

4. An intraoral dental camera assembly comprising:

an elongated instrument body section including a distal camera head fixedly attached thereto;

a flexible protective sheath for loosely covering at least a portion of said body section, including said camera head; and a unitary sleeve member releasably attachable to at least a portion of said body portion for clamping said protective sheath in a predetermined position so as to prevent twisting of said sheath during use, said sleeve member being made from a tubular section of an elastomeric material having an inner dimension which is no larger than an outer diameter of said elongated instrument body to allow form fitting thereto.

5. A camera assembly as recited in claim 4, wherein said gripping handle is disposable.

\* \* \* \* \*